(12) United States Patent
Stuelpnagel et al.

(10) Patent No.: US 6,396,995 B1
(45) Date of Patent: May 28, 2002

(54) METHOD AND APPARATUS FOR RETAINING AND PRESENTING AT LEAST ONE MICROSPHERE ARRAY TO SOLUTIONS AND/OR TO OPTICAL IMAGING SYSTEMS

(75) Inventors: John R. Stuelpnagel, Encinitas; Mark S. Chee, Del Mar; Richard J. Pytelewski, San Diego; Todd Alan Dickinson, San Diego; Gan G. Wang, San Diego, all of CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 09/574,962

(22) Filed: May 19, 2000

Related U.S. Application Data

(60) Provisional application No. 60/135,089, filed on May 20, 1999.

(51) Int. Cl.[7] .................................................. G02B 6/00
(52) U.S. Cl. ........................ 385/136; 385/115; 385/120
(58) Field of Search .............................. 385/14, 52, 65, 385/83, 120, 129, 134–137, 115; 248/74.2, 316.1, 316.5–316.7, 65, 67.7, 70, 74.1; 104/200–202, 214–218; 264/1.1, 1.21–1.29, 1.31–1.38, 1.6–1.8, 1.9, 2.1–2.7

(56) References Cited

U.S. PATENT DOCUMENTS

| | | | | | |
|---|---|---|---|---|---|
| 3,853,658 A | * | 12/1974 | Ney | ............................ | 156/180 |
| 4,046,454 A | * | 9/1977 | Pugh, III | ...................... | 385/59 |
| 4,744,627 A | * | 5/1988 | Chande et al. | ............... | 385/137 |
| 4,973,128 A | * | 11/1990 | Hodges | ....................... | 385/116 |
| 5,369,566 A | | 11/1994 | Pfost et al. | | |
| 5,379,361 A | * | 1/1995 | Maekawa et al. | .............. | 385/65 |
| 5,589,351 A | | 12/1996 | Harootunian | | |

FOREIGN PATENT DOCUMENTS

| | | |
|---|---|---|
| DE | 44 30 621 C1 * | 6/1995 |
| EP | 0 902 271 A2 | 3/1998 |
| GB | 2 315 130 A | 1/1998 |
| GB | 2 315 131 A | 1/1998 |
| GB | 2 315 131 A * | 1/1998 |
| JP | 11271227 | 10/1998 |

* cited by examiner

*Primary Examiner*—Hemang Sanghavi
*Assistant Examiner*—Michelle R. Connelly-Cushwa
(74) *Attorney, Agent, or Firm*—Flehr Hohbach Test Albritton & Herbert LLP

(57) ABSTRACT

A holder for an array of bundles containing multiple fiber optic strands provides a pattern of openings into which one each of each bundle is fit. The openings may (but need not) penetrate the full holder thickness to permit working with bundles from either bundle end. In one embodiment the holder thickness equals the bundle length, and the holder is sized similarly to a microscope slide. An alternative embodiment temporarily retains bundles in a desired registration and subjects the retained bundles to molten material such as wax that is allowed to harden around the bundles and become the holder. A modular holder comprises laminates that each contain parallel grooves sized to receive a bundle. A holder for a single bundle includes cooperating grip-like members, one of which is pivotably attached and biased toward the other member. A common form factor may be used for each holder type to facilitate retaining holders in a common docking station.

24 Claims, 10 Drawing Sheets

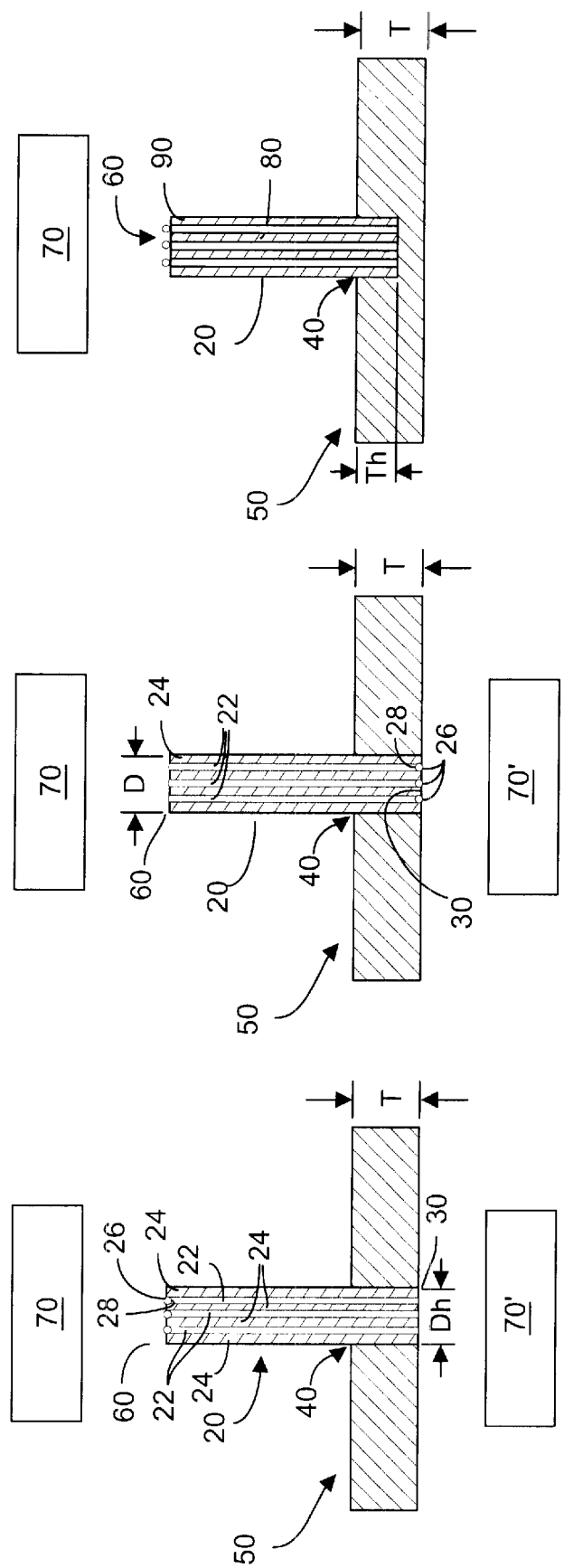

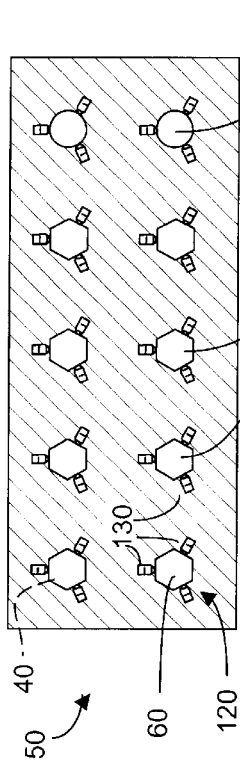
FIG. 5A
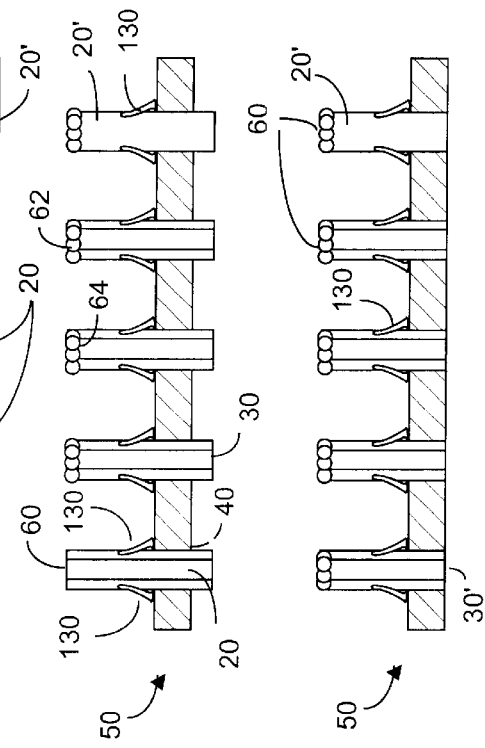
FIG. 5B
FIG. 5C
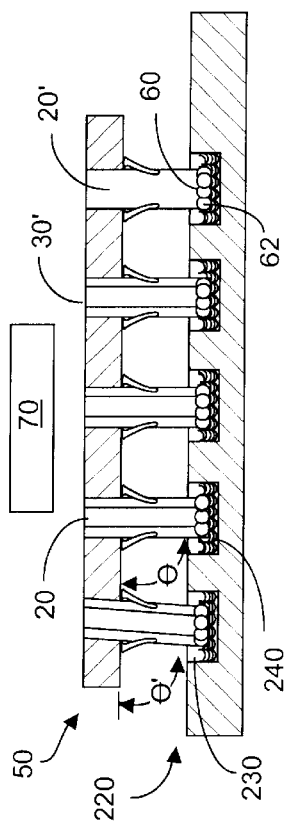
FIG. 5D

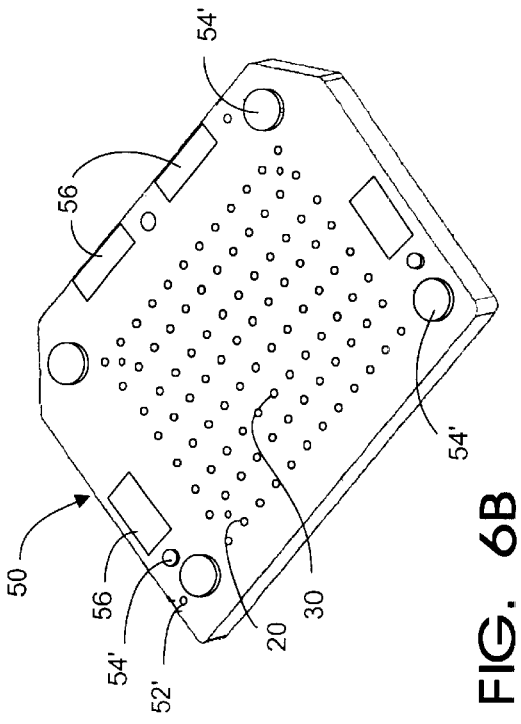
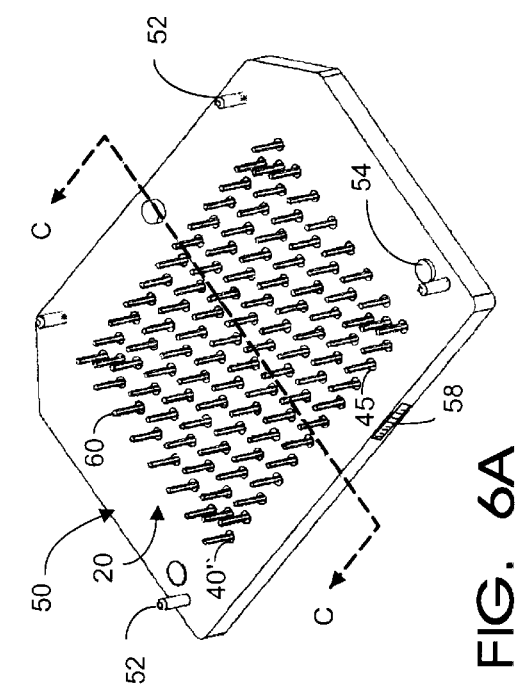
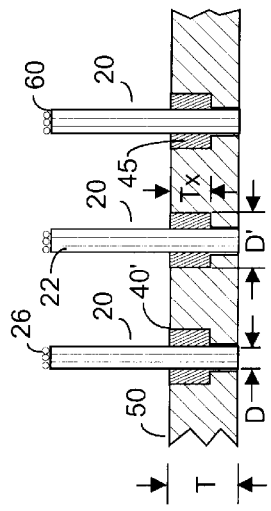
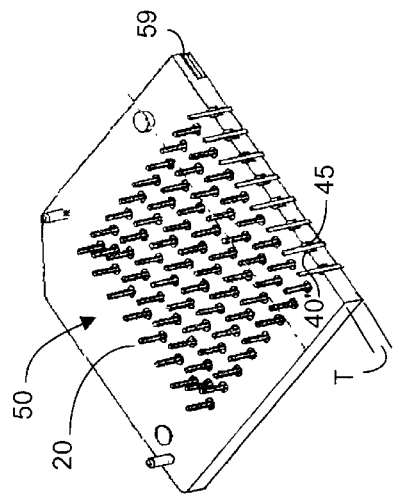
FIG. 6A
FIG. 6B
FIG. 6C
FIG. 6D

METHOD AND APPARATUS FOR RETAINING AND PRESENTING AT LEAST ONE MICROSPHERE ARRAY TO SOLUTIONS AND/OR TO OPTICAL IMAGING SYSTEMS

RELATIONSHIP TO PENDING APPLICATIONS

This application claims priority from U.S. provisional application Ser. No. 60/135,089 filed May 20, 1999 by J. R. Stuelpnagel and M. S. Chee, applicants herein, and entitled "Holder for Probe Arrays".

FIELD OF THE INVENTION

This application relates generally to methods and apparatuses to obtain and analyze optically imaged samples including microbiological samples, and more specifically to methods and apparatuses for retaining at least one and preferably multiple randomly ordered microsphere arrays to solutions and to optical imaging systems for analysis.

BACKGROUND OF THE INVENTION

It is known in the art to use probe arrays and sensors in systems to detect the presence and/or concentration of specific substances in fluids and gases. Many such systems rely on specific ligand/antiligand reactions as the detection mechanism. Pairs of substances (e.g., ligand and antiligands) are known to bind preferentially to each other, but to exhibit little or no binding with other substances.

Many prior art techniques utilize such binding pairs to detect complexes of interest. Often one component of the complex is labeled so as to make the entire complex detectable, using, for example, radioisotopes, fluorescent and other optically active molecules, enzymes, etc. Detection mechanisms utilizing luminescence are especially useful. Within the past decade, considerable development of optical fibers and fiber strands for use in combination with light absorbing dyes for chemical analytical determinations has occurred. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in C.R.C. Critical Reviews In Analytical Chemistry, Vol. 19, 1988, pp. 135–173; Wolfbeis, O. S., "Fiber Optical Fluorosensors In 5 Analytical Chemistry" in Molecular Luminescence Spectroscopy, Methods and Applications (S. G. Schulman, editor), Wiley & Sons, New York (1988); Angel, S. M., Spectroscopy 2 (4):38 (1987); Walt, et al., "Chemical Sensors and Microinstrumentation", ACS Symposium Series, Vol. 403, 1989, p. 252, and Wolfbeis, O. S., Fiber Optic Chemical Sensors, Ed. CRC Press, Boca Raton, Fla., 1991, 2nd Volume.

When using an optical fiber in an in vitro/in vivo sensor, at least one light absorbing dye is located near the fiber distal end. An appropriate source provides light, typically through the fiber proximal end, to illuminate the dye(s). As light propagates along the length of the optical fiber, a fraction of the propagated light exits the distal end and is absorbed by the dye. The light absorbing dye(s) may or may not be immobilized, may or may not be directly attached to the optical fiber itself, may or may not be suspended in a fluid sample containing one or more analyses of interest, and may or may not be retainable for subsequent use in a second optical determination.

Upon being dye absorbed, some light of varying wavelength and intensity returns to be conveyed through the same fiber or through collection fiber(s) to an optical detection system where it is observed and measured. Interactions between the light conveyed by the optical fiber and the properties of the light absorbing dye can provide an optical basis for both qualitative and quantitative determinations.

Many different classes of light absorbing dyes are conventionally employed with bundles of fiber strands and optical fibers for different analytical purposes. The more common dye compositions that emit light after absorption are termed "fluorophores", while dyes that absorb and internally convert light to heat (rather than emit as light) are termed "chromophores."

Fluorescence is a physical phenomenon based upon the ability of some molecules to absorb light (photons) at specified wavelengths, and then emit light of a longer wavelength and at a lower energy. Substances able to fluoresce share a number of common characteristics: the ability to absorb light energy at one wavelength $\lambda_{ab}$, reach an excited energy state, and subsequently emit light at another light wavelength $\lambda_{em}$. Absorption and fluorescence emission spectra are unique for each fluorophore and are often graphically represented as two slightly overlapping separate curves.

The same fluorescence emission spectrum is generally observed irrespective of the wavelength of the exciting light. Thus, within limits, the wavelength and energy of the exciting light may be varied, but the light emitted by the fluorophore will consistently exhibit the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., Principles of Fluorescence Spectroscopy, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in Chemical Analysis, vol. 77, Wiley & Sons, Inc., 1985; The Theory of Luminescence, Stepanov and Gribkovskii, Iliffe Books, Ltd., London, 1968.

In contrast to fluorescence emitting materials, substances that absorb light but do not fluoresce usually convert the light into heat or kinetic energy. The ability to internally convert the absorbed light identifies the dye as a "chromophore." Dyes that absorb light energy as chromophores do so at individual wavelengths of energy and are characterized by a distinctive molar absorption coefficient at that wavelength. Chemical analysis employing fiber optic strands, and absorption spectroscopy using visible and ultraviolet light wavelengths in combination with the absorption coefficient can determine concentration for specific analyses of interest using spectral measurement. The most common use of absorbance measurement via optical fibers is to determine concentration, which is calculated in accordance with Beers' law. Accordingly, at a single absorbance wavelength, the greater the quantity of the composition that absorbs light energy at a given wavelength, the greater the optical density for the sample. In this fashion, the total quantity of light absorbed directly correlates with the quantity of the composition in the sample.

Many recent improvements in the use of optical fiber sensors in qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations, and for applications such as pH measurement, oxygen detection, and carbon dioxide analyses. These developments are exemplified by the following publications: Freeman, et al., Anal Chem. 53:98 (1983); Lippitsch et al., Anal. Chem. Acta. 205: 1, (1988); Wolfbeis et al., Anal. Chem. 60:2028 (1988); Jordan, et al., Anal. Chem. 59:437 (1987); Lubbers et al.e, Sens. Actuators 1983; Munkholm et al., Talanta 35:109 10 (1988): Munkholmetal., Anal. Chem. 58:1427(1986); Seitz, W. R., Anal. Chem. 56:16A–34A (1984); Peterson, et al., Anal. Chem. 52:864 (1980): Saari, et al., Anal. Chem. 54:821 (1982); Saari, et al., Anal. Chem. 55:667 (1983); Zhujun et al., Anal. Chem. Acta. 160:47 (1984); Schwab, et al., Anal. Chem. 56:2199 (1984); Wolfbeis, O. S., "Fiber Optic Chemical Sensors", Ed. CRC Press, Boca Raton, Fla., 1991, 2nd Volume; and Pantano, P., 15 Walt, D. R., Anal. Chem., 481A–487A, Vol. 67, (1995).

More recently, fiber optic sensors have been constructed that permit the use of multiple dyes with a single, discrete fiber optic bundle. For example, U.S. Pat. Nos. 5,244,636 , 5,250,264, and 5,320,814 to Walt et al. disclose systems for affixing multiple, different dyes on the distal end of a fiber optic bundle. Applicants refer to and incorporate herein by reference each said patent to Walt et al. The configurations disclosed in these patents to Walt et al. enable separate optical fibers of the bundle to optically access individual dyes. So doing avoids the problem of deconvolving the separate signals in the returning light from each dye. This problem can otherwise arise when signals from two or more dyes are combined, with each dye being sensitive to a different analyte, where there is significant overlap in the dyes' emission spectra.

U.S. Pat. No. 6,023,540 and pending U.S. patent application Ser. No. 09/151,877 describe array compositions that utilize microspheres or beads on a surface of a substrate. Such substrate can be the terminal end of a fiber optic bundle, with each individual fiber comprising a bead containing an optical signature. Since the beads are deposited on the substrate surface randomly during fabrication, a unique optical signature is needed to "decode" the array. Stated differently, after the array is fabricated, a correlation between location of an individual site on the array with the bead or bioactive agent at that particular site can be made. This implies that the beads may be randomly distributed on the array, an advantageously fast and inexpensive process when compared to an in situ synthesis or spotting techniques of the prior art. Once the array is loaded with the beads, the array may be decoded, or can be used with full or partial decoding occurring after testing.

A practical problem associated with the use of such probe arrays is how to properly retain and present the arrays to solutions and to optical imaging systems. Ideally each fiber optic bundle should be maintained parallel to each other, and normal to a holding mechanism to ensure accurate registration when optically imaging. Unfortunately prior art holding mechanisms do not readily meet this goal. Further, in prior art holders, if a fiber optic bundle becomes damaged or misaligned it is often necessary to discard the entire array of fiber optic bundle.

Thus there is a need for a mechanism to hold at least a single fiber optic bundle array and preferably a plurality of arrays in good registration. Such registration should be maintainable by the holder mechanism both during final machining of the fiber optic bundle ends, e.g., when the bundle ends are polished and loaded with beads or other analytic means, and during analysis. Preferably such mechanism should permit replacement of individual fiber optic bundles as may become necessary. Further, the holder mechanism should be straightforward and relatively inexpensive to produce The present invention provides such holders and methods for using same.

SUMMARY OF THE INVENTION

In a first aspect, the present invention provides a holder defining at least one opening sized to engage and retain an end portion of a single fiber optic bundle or an array of such arrays. Each fiber optic bundle typically comprises a great many individual fiber optic strands that form an array. The holder typically is planar with spaced-apart upper and lower surfaces and may be made from metal, glass, ceramic, plastic, or epoxy (including thermosetting epoxy), among other materials. In cross-section, the fiber optic retaining opening is normal to a base plane of holder such that a length of fiber optic is retained in the holder perpendicular to the base plane. Preferably the holder will define an array of openings such that a plurality of fiber optic bundles may be retained in a preferred perpendicular orientation relative to the base. Since each retained bundle comprises many fiber optic strands, the holder is said to retain an array of arrays. The holder configuration ensures a proper registration relationship among the retained bundles, to solution containing wells and/or to an optical imaging system used to image the retained bundles. If desired, the holder may retain adjacent bundles such that multiple bundles can be processed within one well.

The opening in the base may be formed completely through the thickness of the holder, in which case a light source used for imaging may be presented from beneath the base or from above the base, at either the proximate or distal end of the retained fiber optic. On the other hand, if the optical system will be disposed above the base, the length of the base opening may be less than the base thickness. Individual bundles may be removed from the holder and replaced, if necessary, without discarding the entire array of arrays.

The holder may be sized similarly to a microscope slide, and the openings formed completely through the holder thickness. In this embodiment, the length of the retained fiber optics is made equal to this holder thickness such that the upper and lower end surface of each fiber optic bundle is respectively flush with the upper and lower surface of the holder. The holder, which may be formed from glass, or stainless steel, among other materials, may be imaged using a microscope, or scanning systems.

In an alternative embodiment, the bundle retaining openings are stepped to surround the retained bundle end with an annular region that is filled with a potting compound. Yet another embodiment surrounds each bundle retaining opening with at least one biased prong-like projection and preferably several such projections to bias or urge and to help maintain the retained bundle in an upright, perpendicular, disposition relative to a plane of the holder. In this embodiment the holder may, but need not, be formed from an injection molded plastic, and the retaining prong or prongs may be integrally molded with the base, or may be discrete components that are attached during formation of the holder.

In another embodiment, the array of fiber optic bundles are initially retained in proper registration in a temporary holder, and are then immersed in molten material such as wax, which is allowed to harden and form around the array of arrays. The hardened wax forms a semi-permanent fiber optic bundle holder, and the temporary holder is removed. The fiber optic bundles so retained by the wax may be lapped and polished, loaded with beads or otherwise treated, and placed into a target analyte-containing solution, and imaged.

The holder may be formed modularly as a laminated structure from planar modules that define grooves into which each bundle is inserted. A plurality of such modules are then assembled in sandwich fashion and held together with screws or the like. The distal ends of the retained bundles may be flush with or project from a face of the modular holder. Such modular holder may be used as an actual holder, or may be used as a temporary holder to facilitate placing bundle ends in a plate-like holder with bundle-retaining openings, or for securing the bundles in a wax holder as described herein.

Features from one holder embodiment may be combined with features from another embodiment. For example, prong-type holders may include through openings sized to frictionally retain a fiber optic bundle, which holes may include counter-bored regions or draft-angled surface regions, or conical shaped regions. These expanded regions can help align and retain the bundles before application of adhesive or potting compound to more permanently retain the bundles in the desired perpendicular registration. Alternatively, bundle ends may be press-fit, or retained within the holder using a controlled melting process.

An alternative embodiment provides a holder intended to retain a single bundle, which holder may be used in an optical imaging system. The holder is generally planar and includes a fixed member and a movable member that is biasedly urged to pivot towards the fixed member. When the two members are biased towards each other they define a gap sized to compressively retain a single fiber optic bundle from at least two sides. The form factor of the holder preferably is similar to that of embodiments intended to hold multiple bundles such that a single docking-type station may be used to retain each type of holder, for example during optical imaging.

Bundles retained in a holder according to the present invention are retained in registration suitable for exposing bundle ends to wells containing solutions, and/or for optical imaging, in situ or otherwise. Bundles may be attached to a holder, according to the present invention, at various process steps, including assembly of the array of arrays, before or after bundle end polishing, before or after bundle end etching, before or after insertion into test solutions, or before imaging or other analytical read-out process. In whatever mode of use, the holder provides a convenient and protective tool to retain an array of fiber optic bundles (or simply one such bundle) for handling, including handling during the various process and analytical steps. During the various process and analytic steps, the holder retains the bundles in a desired and consistent spatial registration, and further protects at least the retained bundle end from damage and from dust. The holder may be removed and reinserted into a docking station at various process steps, while consistently maintaining registration among the retained array of bundles. If desired, a surface of the holder may contain a barcode or other identification to uniquely identify the array of bundles that is retained.

Other features and advantages of the invention will appear from the following description in which the preferred embodiments have been set forth in detail, in conjunction with the accompanying drawings.

BRIEF DESCRIPTION OF THE DRAWINGS

FIGS. 2A and 2B are cross-sections of a through-opening in a holder, according to the present invention;

FIG. 2C is a cross-section of a partial opening in a holder, according to the present invention;

FIG. 5A is a top plan view of fiber optic bundles retained in a fiber optic bundle holder that includes biased alignment elements, according to the present invention;

FIG. 5B is a side cross-sectional view of the holder and bundles shown in FIG. 5A, according to the present invention;

FIG. 5C depicts the holder and bundles shown in FIG. B after machining of the retained bundle ends, according to the present inventions;

FIG. 5D depicts cooperation between fiber optic bundles retained in the holder of FIG. 5A and a well plate, depicting allowable alignment skew, according to the present invention;

FIG. 6A is a top perspective view of fiber optic bundles retained with potting compound in a holder, according to the present invention;

FIG. 6B is a bottom perspective view of the holder shown in FIG. 6A, according to the present invention;

FIG. 6C is a perspective cross-section view of the holder of FIG. 6A taken along section line C—C, according to the present invention;

FIG. 6D is a detailed cross-sectional view of a portion of the holder of FIG. 6A, according to the present invention;

DETAILED DESCRIPTION OF THE PREFERRED EMBODIMENTS

Figure 1:
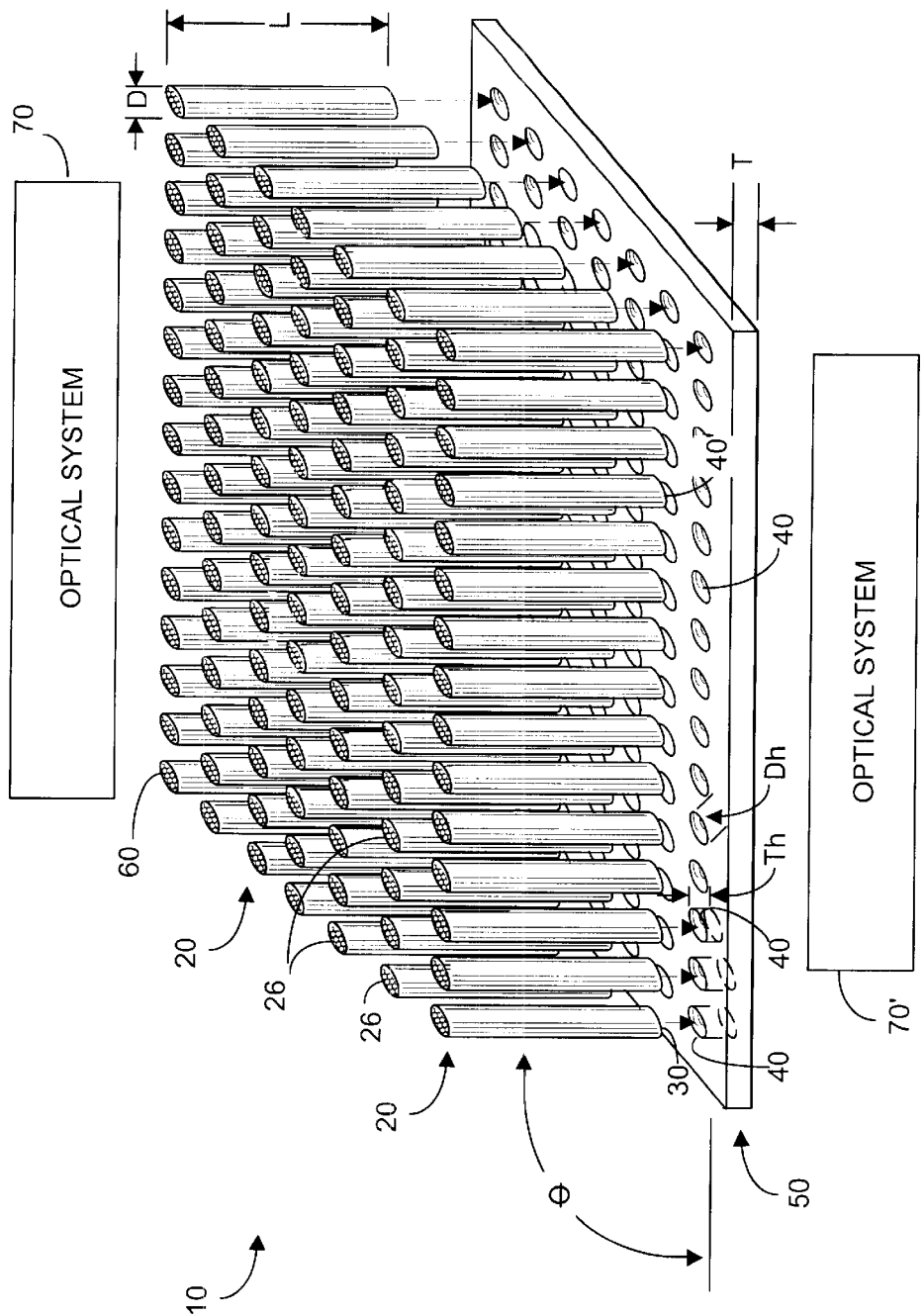
FIG. 1 is a perspective view of an array of fiber optic bundles to be retained in a holder, according to the present invention.

The present invention is directed to a variety of apparatus to hold bioactive agent arrays, particularly nucleic acid arrays, during assays. In general, the invention draws on previous work describing microsphere arrays; see PCTs US98/21193, PCT US99/14387 and PCT US98/05025; WO98/50782; and U.S. Ser. Nos. 09/287,573, 09/151,877, 09/256,943, 09/316,154, 60/11,323, 09/315,584; all of which are expressly incorporated by reference, which describe novel compositions utilizing substrates with microsphere arrays.

The present invention is generally based on previous work comprising a bead-based analytic chemistry system in which beads, also termed microspheres, carrying different chemical functionalities are distributed on a substrate comprising a patterned surface of discrete sites that can bind the individual microspheres. Since the beads are generally put onto the substrate randomly, the previous work relied on the incorporation of unique optical signatures, generally fluorescent dyes, that could be used to identify the chemical functionality on any particular bead. This allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art. That is, as will be appreciated by those in the art, the placement of the bioactive agents is generally random, and thus a coding/decoding system is required to identify the bioactive agent at each location in the array. This may be done in a variety of ways, as is generally described in WO99/67641 and an application filed on Apr. 21, 2000, entitled "Detection of Nucleic Acid Reactions on Bead Arrays" (no serial number received yet) both of which are hereby expressly incorporated by reference. These methods include a) the use of decoding binding ligands (DBLs), generally directly labeled, that binds to either the bioactive agent or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites; c) selective decoding, wherein only those beads that bind to a target are decoded; or d) combinations of any of these. In some cases, this decoding may occur for all the beads, or only for those that bind a particular target analyte. Similarly, this may occur either prior to or after addition of a target analyte.

Once the identity of the bioactive agent and its location in the array has been fixed, the array is exposed to samples containing the target analytes, this can be done prior to or during the analysis as well. The target analytes will bind to the bioactive agents as is more fully outlined below, and results in a change in the optical signal of a particular bead.

Accordingly, the present invention provides array compositions comprising at least a first substrate with a surface comprising individual sites. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made.

Preferred ranges for very high density arrays are from about 10,000,000 to about 2,000,000,000 (all numbers are per square cm), with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 $\mu$m or less (with beads of 200 nm possible) can be used, and very small fibers are known, it is possible to have as many as 250,000 or more (in some instances, 1 million) different fibers and beads in a 1 mm2 fiber optic bundle, with densities of greater than 15,000,000 individual beads and fibers (again, in some instances as many as 25–50 million) per 0.5 cm2 obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the association of beads at any position. That is, the surface of the substrate is modified to allow association of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to associate, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic association of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow association of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers IN is a helpful guide.

The beads need not be spherical; irregular particles may be used. In addition, the beads may be porous, thus increasing the surface area of the bead available for either bioactive agent attachment or IBL attachment. The bead sizes range from nanometers, i.e. 100 nm, to millimeters, i.e. 1 mm, with beads from about 0.2 micron to about 200 microns being preferred, from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occur-ing proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agent s are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid"or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

In a preferred embodiment, the bioactive agents are libraries of clonal nucleic acids, including DNA and RNA. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the beads. For example, cloned nucleic acids can be derivatized, for example with one member of a binding pair, and the beads derivatized with the other member of a binding pair. Suitable binding pairs are as described herein for IBL/DBL pairs. For example, the cloned nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, special methods are required to decode clonal arrays, as is more fully outlined below.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarily need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term 'target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads.

As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, $\alpha$-haloacetyls, and pyridyl disulfides (see for example the 1994 Pierce Chemical Company catalog, technical section on cross-linkers, pages 155–200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155–200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., Critical Rev. Therapeutic Drug Carrier Systems, 7(4):275–308 (1991), expressly incorporated herein). Proteinaceous candidate agents may also be attached using other techniques known in the art, for example for the attachment of antibodies to polymers; see Slinkin et al., Bioconj. Chem. 2:342–348 (1991); Torchilin et al., supra; Trubetskoy et al., Bioconj. Chem. 3:323–327 (1992); King et al., Cancer Res. 54:6176–6185 (1994); and Wilbur et al., Bioconjugate Chem. 5:220–235 (1994), all of which are hereby expressly incorporated by reference). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant) –0.02%, and rinsed again with a pH 7.7 PBS plus 0.01% tween 20. Finally, the enzyme is added to the solution, preferably after being prefiltered using a 0.45 $\mu$m amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$–$10^{-6}$ M$^{-1}$, with less than about $10^{-5}$–$10^{-9}$ M$^{-1}$ being preferred and less than about $10^{-7}$–$10^{-9^6}$ M$^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion- metal ion ligands or chelators pairs are also useful. Antigen-antibody pairs, enzymes and substrates or inhibitors, other protein-protein interacting pairs, receptor-ligands, complementary nucleic acids (including nucleic acid molecules that form triple helices), and carbohydrates and their binding partners are also suitable binding pairs. Nucleic acid—nucleic acid binding proteins pairs are also useful, including single-stranded or double-stranded nucleic acid binding proteins, and small molecule nucleic acid binding agents. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the bioactive agent are the same moiety; thus, for example, as outlined herein, particularly when no optical signatures are used, the bioactive agent can serve as both the identifier and the agent. For example, in the case of nucleic acids, the bead-bound probe (which serves as the bioactive agent) can also bind decoder probes, to identify the sequence of the probe on the bead. Thus, in this embodiment, the DBLs bind to the bioactive agents. This is particularly useful as this embodiment can give information about the array or the assay in addition to decoding. For example, as is more fully described below, the use of the DBLs allows array calibration and assay development. This may be done even if the DBLs are not used as such; for example in non-random arrays, the use of these probe sets can allow array calibration and assay development even if decoding is not required.

In a preferred embodiment, the microspheres do not contain an optical signature. That is, as outlined in U.S. Ser. Nos. 08/818,199 and 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Thus, the present invention does not rely solely on the use of optical properties to decode the arrays. However, as will be appreciated by those in the art, it is possible in some embodiments to utilize optical signatures as the sole or additional coding method. Thus, for example, as is more fully outlined below, the size of the array may be effectively increased while using a single set of decoding moieties in several ways, one of which is the use in combination with optical signatures one beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0"(IBL is absent). A 10 bit binary code has 210 possible variants However, as is more fully discussed below, the size of the array may be further increased if another parameter is included such as concentration or intensity; thus for example, if two different concentrations of the IBL are used, then the array size increases as 3n. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

Once the microspheres comprising the candidate agents and the unique IBLs are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target analytes, prior to the addition of the beads to the substrate; after addition and assay, the array may be decoded. This is particularly preferred when the sample comprising the beads is agitated or mixed; this can increase the amount of target analyte bound to the beads per unit time, and thus (in the case of nucleic acid assays) increase the hybridization kinetics. This may find particular use in cases where the concentration of target analyte in the sample is low; generally, for low concentrations, long binding times must be used.

In addition, adding the beads to the assay mixture can allow sorting or selection. For example, a large library of beads may be added to a sample, and only those beads that bind the sample may be added to the substrate. For example, if the target analyte is fluorescently labeled (either directly (for example by the incorporation of labels into nucleic acid amplification reactions) or indirectly (for example via the use of sandwich assays)), beads that exhibit fluorescence as a result of target analyte binding can be sorted via Fluorescence Activated Cell Sorting (FACS) and only these beads added to an array and subsequently decoded. Similarly, the sorting may be accomplished through affinity techniques; affinity columns comprising the target analytes can be made, and only those beads which bind are used on the array. Similarly, two bead systems can be used; for example, magnetic beads comprising the target analytes can be used to "pull out"those beads that will bind to the targets, followed by subsequent release of the magnetic beads (for example via temperature elevation) and addition to an array.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for association of the beads. This may be done in a variety of buffers, including aqueous and organic solvents, and mixtures. The solvent can evaporate, and excess beads removed.

In a preferred embodiment, when non-covalent methods are used to associate the beads to the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differnetial affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to associate the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface. Decoding generally proceeds as outlined in WO99/67641 and an application filed on Apr. 21, 2000, entitled "Detection of Nucleic Acid Reactions on Bead Arrays" (no serial number received yet) both of which are hereby expressly incorporated by reference.

Turning now to the preferred embodiments and the figures, FIG. 1 depicts a system 10 in which at least one and typically a plurality of fiber optic bundles (or stalks or probes) 20 are retained at a lower stalk end 30 in an opening 40 formed in a holder 50, according to the present invention. It is the function of holder 50 to retain each bundle 20 in an upright disposition (in the geometry of FIG. 1) such that the longitudinal axis of the stalk is perpendicular or normal to a plane of holder 50. A substantially perpendicular orientation between bundles 20 and the plane of holder 50 helps ensure registration between each bundle end 60 (or indeed end 30) and an optical system 70 (or 70') used for imaging. For ease of illustration, FIG. 1 depicts bundles 20 spaced-apart from their respective retaining openings 40 in holder 50.

Each fiber optic bundle 20 will generally comprise a plurality of individual fiber optic strands 22, often thousands of strands, and each strand in a bundle will be (but need not be) surrounded by cladding material 24 (see FIGS. 2A–2C). In a manner known to those skilled in the relevant art, the ends of the bundles are machined or otherwise processed. Typically a free end of each strand 22 is loaded with a bead 26, deposited in a generally concave well 28 formed in the strand end. Ideally, a single bead is deposited in a well region formed at the free end of an individual strand within a bundle 20. Each bundle 20 may be said to comprise an array of detectors, and holder 50 may properly be said to retain an array of arrays. It is common in the art to deal with an array of 96 bundles, but as suggested by FIG. 1, the present invention may hold a larger (or a smaller) number of bundles. Indeed standard microtiter plates are fabricated with 96, 384, or 1,536 wells, and various embodiments of the present invention can registerably retain one or more fiber optic bundles in similar densities. If desired, holders according to the present invention can retain bundles such that the beaded ends of more than one fiber optic bundle can be accommodated in a single well.

As shown in FIG. 1, holder 50 preferably is planar with upper and lower surfaces spaced-apart a distance or thickness T that may be in the range of perhaps 0.5 mm to 1.5 cm, although other thickness values may instead be used. Holder 50 may but need not be an optically transparent and can be made from metal, glass, ceramic, plastic, epoxy including thermosetting epoxy, or other material. As noted, analysis typically involves exposing beaded fiber optic bundle ends to a solution and then imaging the bundle beaded ends with a fluorescent light source. Thus, it is preferred that holder 50 be made of a material that emits little or no background fluorescence, which emissions could degrade the detected signal-to-noise ratio.

As best seen in FIGS. 2A and 2C, the depth Th of openings 40 into the thickness T of holder 50 may be a fraction less than one. Thus, in FIG. 2A at least one opening 40 is formed completely through the holder thickness T, e.g., Th=T, whereas in FIG. 2C at least one opening 40 is formed partially through the holder thickness T, e.g., Th<T. In the embodiment of FIG. 2A, imaging of bundle 20 may occur from above using system 70 and/or from below using system 70'. By contrast, the embodiment of FIG. 2C permits imaging only from above, using system 70, and will involve light reflections from end 60 of bundle 20.

The diameter Dh of a given opening 40 is at least as large as diameter D of the individual bundle 20 to be retained. Bundle diameters D may vary from perhaps 0.1 mm (a size comprising perhaps 1,000 separate strands) to perhaps 15 cm. A commonly used stalk diameter is D≈1.2 mm, a size comprising perhaps 44,000 separate strands. Details as to the composition of stalks 20 may be found in the literature cited, including the cited U.S. patents to Walt, et al., and thus a further description of stalks 20 will not be presented herein. The length L of a typical bundle can also vary from as short as the thickness T of base 50 (see embodiment of FIG. 3A) to perhaps 1" or 2.5 cm, or longer. One end 30 of each bundle 20 is retained within an opening 40 in holder 50. Retention can result from friction, e.g., Dh≈D, or can result from the use of adhesions, thermal bonding, wax bonding, controlled melting, among other bonding substances or bonding techniques. As noted, a goal is to maintain a parallel configuration among bundles 20, and to maintain the longitudinal axis of each bundle substantially perpendicular to the plane of base 50, such that θ≈90°, as shown in FIG. 1. Ensuring perpendicularity of bundles helps ensure that the planar end of each bundle, e.g., ends 60 in FIG. 1, will remain in substantial registration with solution-containing wells, and with optics associated with optical system 70 (or 70').

Figure 3A:
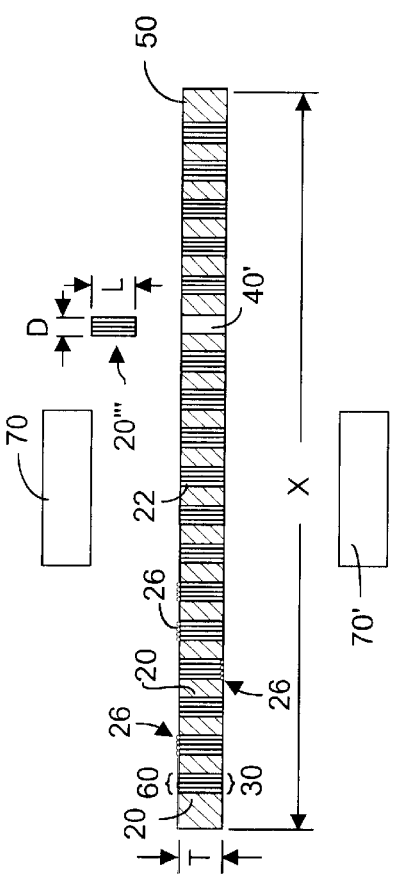
FIG. 3A is a perspective view of a microscope slide-like holder and retained fiber optic bundles, according to the present invention.
Figure 3B:
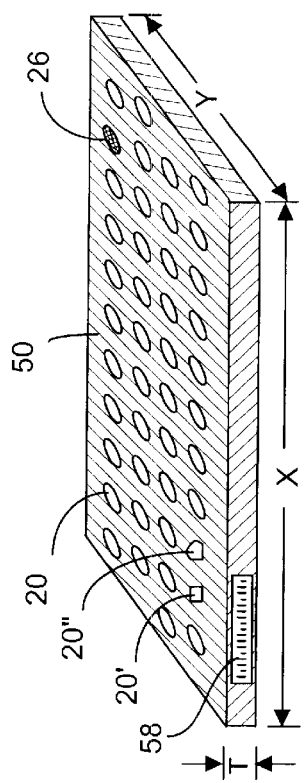
FIG. 3B is a cross-section of the embodiment of FIG. 3A showing one fiber optic bundle removed and showing imaging systems, according to the present invention.

The embodiment shown in FIGS. 3A and 3B ensures excellent registration in that there is no distal or unsupported bundle end to perhaps move out of registration due to an overly long value of L. As shown in FIG. 3B by bundle 20''', which is depicted as removed from its associated through opening 40', bundle length L≈T, e.g., the surface of bundle upper end 60 is substantially flush with the upper surface of holder 50, and the surface of bundle lower end 30 is substantially flush with the lower surface of holder 50. If desired, however, holders may be provided in which T≧L.

As in the embodiment of FIG. 1, holder 50 may be constructed from almost any material, but preferably will be a rigid and durable material that does not fluoresce. Without limitations, glass or stainless steel are good materials from which to fabricate holder 50 as shown in FIGS. 3A and 3B. Glass is a preferred material as it polishes compatibly with the fiber optic bundles. In the embodiment of FIGS. 3A and 3B, holder thickness T may be about 0.5 mm to about 5 mm, dimension X is perhaps 1" (2.5 cm) and dimension Y is perhaps 3" (7.5 cm), or approximately the configuration of a standard microscope slide.

It is important that holder 50 maintain registration between the various retained bundles. However the cross-sectional shape of any or all of the bundles is not critical. Thus, in FIG. 3A, bundle 20' is shown as being non-circular, whereas bundle 20" is shown as being partially curved and partially not curved. For ease of illustration, in FIGS. 3A and 3B an array comprising 66 bundles 20 is shown, in which each bundle comprises four separate strands 22, each of which may include one bead 26. Of course in reality the array may be substantially larger than 66 bundles, and a bundle may have many thousands of individual strands, beaded or otherwise. Note that the pattern of the array in FIG. 3A is staggered relative to the more orderly row-column pattern shown in FIG. 1. Thus it is understood that the present invention is not limited in the pattern arrangement of the arrayed bundles it will retain.

Figure 3C:
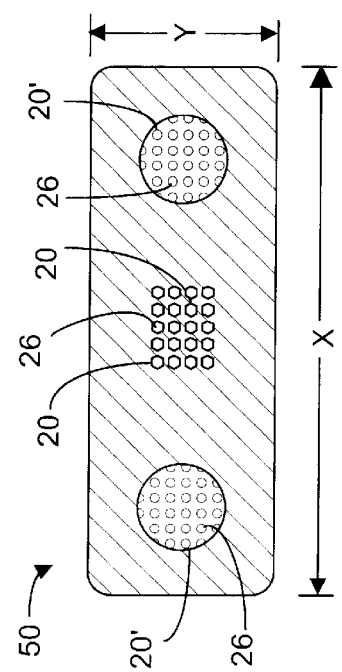
FIG. 3C is a top plan view of a microscope slide-like holder showing two retained large fiber optic bundles, and several smaller hexagon shaped fiber optic bundles, according to the present invention.

FIG. 3C depicts a holder 50 that preferably has a form factor similar to a microscope slide, e.g., dimension X is about 3" or about 7.5 cm, dimension Y is about 1" or 2.5 cm, and thickness T (measured into the plane of the figure) is perhaps 0.04" or around 1 mm, although different X,Y, and T dimensions could be used. The embodiment of FIG. 3C depicts that holders according to the present invention need not retain identically sized fiber optic bundles 20, 20'. In the embodiment shown, bundles 20 are hexagon shaped in cross-section, whereas bundles 20' are substantially larger and are circular shaped in cross-section. For example, each of the six flat sides of bundles 20 might be 0.03" or 0.75 mm in length, whereas bundles 20' might be 0.8" or about 2 cm in diameter. In the embodiment shown, the thickness T of the preferably steel holder 50 approximates the length L of the retained bundles 20, 20'. As indicated by FIG. 3C, in general the individual fiber optic strands within a bundle will have a bead 26 at one strand surface, The embodiments of FIGS. 3A–3C are especially robust, and the slide-like form factor allows holder 50 and its retained bundles 20 and/or 20' to be examined using a system 70 or 70' that may include a microscope or a standard optical scanner. The familiar slide-like form factor makes promotes safe handling of the retained bundles, and can minimize contamination of the bundle ends. Further, providing a rigid holder 50 permits reusing the holder many times, simply by removing the bundles after analysis has been completed and filling the empty holes 40 with fresh bundles. Note that a barcode 58 or the like may be attached to the holder for use in identifying the retained bundles.

Figures 4A, 4B:
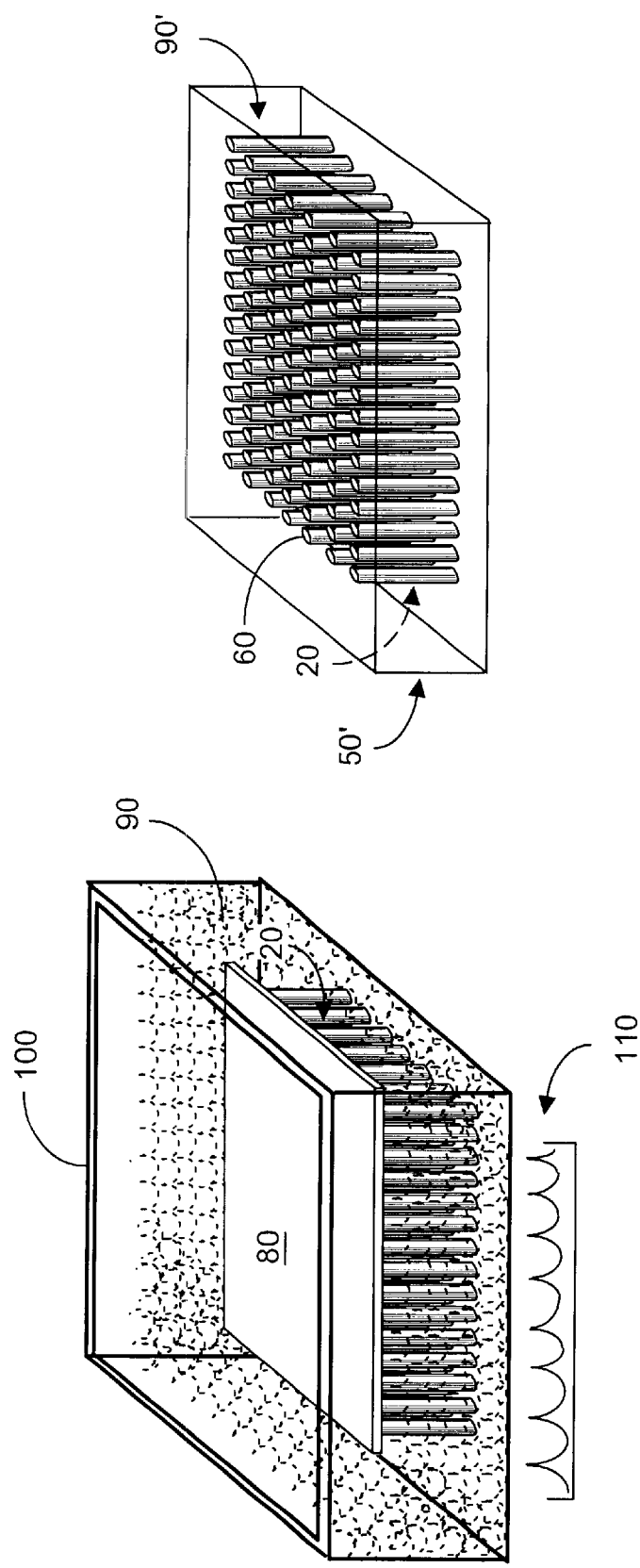
FIG. 4A depicts formation of a fiber optic bundle holder from molten wax, according to the present invention.
FIG. 4B is a perspective view of a wax fiber optic bundle holder resulting from the method shown in FIG. 4A, according to the present invention.

In the embodiments described thus far, the array holder 50 was fabricated from a rather durable material. By contrast, FIGS. 4A and 4B depict a holder 50' that may be made from a readily meltable material such as wax. FIG. 4A depicts a plurality of fiber optic bundles 20 (which may be identical to bundles 20 described with respect to FIGS. 1–3B) retained at one bundle end within a temporary holder 80. Temporary holder 80 may in fact be similar to holder 50 as shown in FIG. 1, and temporarily retains bundles 20 in a desired array pattern. FIG. 4A depicts the array of bundles 20 being immersed in a molten bath of heated wax 90 (or other meltable material), depicted as phantom waves. For ease of illustration, FIG. 4A depicts the molten wax (or other material) 90 contained within a transparent walled aquarium-like container or mold structure 100, shown being heated by a heater mechanism 110. Material 90 is preferably a high temperature wax that melts at perhaps 250° F., although other materials besides wax might instead be used.

It is understood that container 100 may take any shape, and that heating mechanism 110 may be implemented in a variety of fashions. However it is the function of container 100 and heating mechanism 110 to create and retain a bath of molten wax 90 into which at least those portions of the array of bundles 20 projecting from temporary holder 80 may be immersed or submerged. For ease of illustration FIG. 4A depicts fiber optic bundles (or probes) 20 as being submerged in the molten wax almost to the level of their base ends, which are retained by temporary holder 80.

Figure 4C:
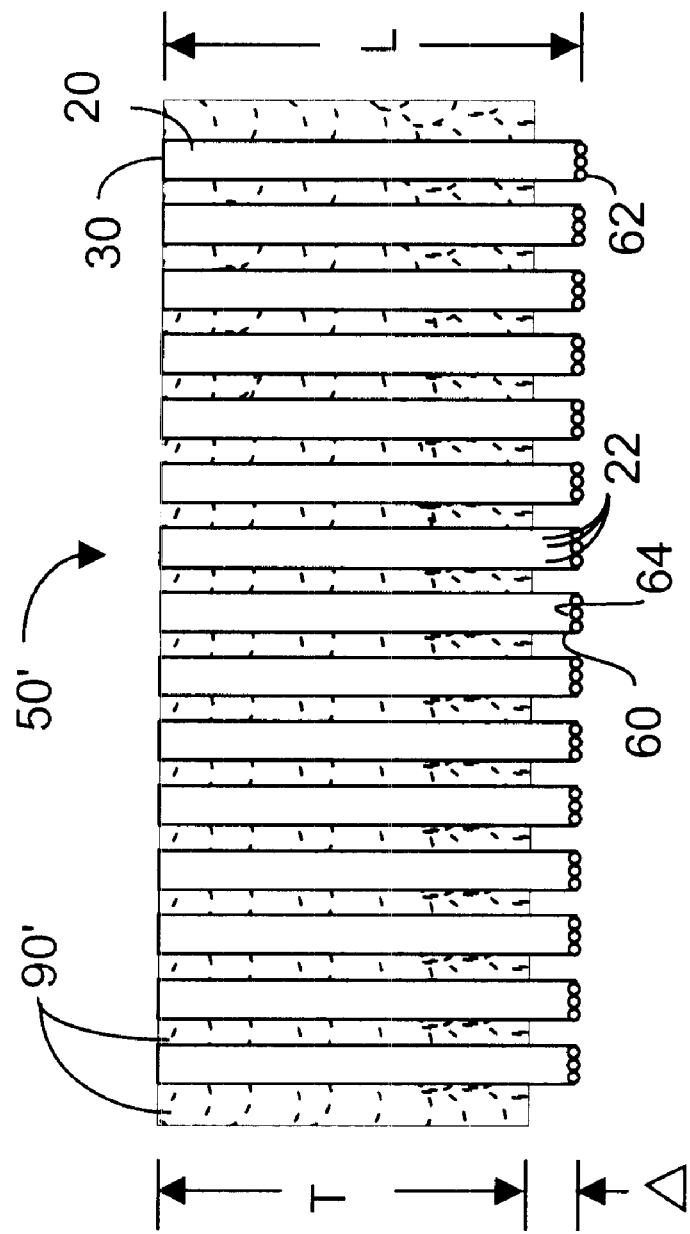
FIG. 4C is a cross-section view of a wax fiber optic bundle holder resulting from the method shown in FIG. 4A, according to the present invention.

The molten wax will fill the space between individual bundles 20. The heat source 110 is turned off and the wax is allowed to harden, and the temporary holder 80 is removed. FIG. 4B depicts the resultant configuration, namely a holder 50' comprised of hardened wax 90'. Bundles 20 are imbedded within the wax holder 50', for at least a fraction of the length L of the bundles. As shown in FIG. 4C, if the spaced-apart thickness of wax holder 50' is T, a fraction Δ of each probe will emerge from the holder, where Δ=(L−T). If desired, however, the bundle length L and the wax holder thickness T could be equal, similar to the configuration of FIGS. 3A and 3B.

The exposed ends 60 of the bundles 20 next are machined or processed, typically by lapping and polishing to planarize the surface of the ends. For ease of understanding, individual fiber strands 22 comprising a bundle 20 are not drawn separately. Concave well regions 64 may be formed in the surface of exposed ends 60 of each strand 22, and a bead 62 deposited in each well, or into a substantial number of the wells. The resultant configuration is what is shown in FIG. 4C, wherein the wax probe holder 50' retains a plurality of fiber optic bundles 20, each bundle comprising perhaps thousands of fiber optic strands 22, each strand (ideally) loaded with a bead 62.

Note that the individual bundles 20 are retained in tight registration with each other by the solidified wax 90'. The longitudinal axis of each bundle will remain substantially parallel to each other, and substantially perpendicular to the plane of the top surface (in the orientation of FIG. 4C) of holder 50'. An advantage of the wax holder shown in FIGS. 4B and 4C is that individual bundles 20 may be removed and replaced, if necessary. For example, one or more bundles might become damaged. Rather than discard the entire array retained by holder 50', the damaged bundles may be removed by heating the wax surrounding the bundles in question. For example, a thin walled hollow tube, whose inner diameter exceeds the outer diameter D of a the bundle to be removed, can be heated and pushed into and through the wax probe, to surround the bundle in question. This localized heating enables the damaged bundle to be removed and replaced with a new or different bundle, around which molten wax can then be deposited to retain the replacement bundle within holder 50'.

FIG. 5A is a top plan view of a holder 50 that places a bias alignment mechanism 120 adjacent the perimeter of each opening 40, to promote a vertical alignment between the longitudinal axis of a fiber optic bundle 20 or 20' held in or by the opening. Preferably bias alignment mechanism 120 includes at least one and preferably three prong-like retainer elements 130, disposed symmetrically about opening 40. Thus, if two retainer elements are provided they will be 180° apart from each other, especially if the retained bundle is hexagonal in cross-section, if three elements are provided they will be 120° apart, and so forth. Preferably holder 50 is fabricated from an injection molded plastic, such that retainer elements 130 may be formed integrally from the same material as the base portion 50. Alternatively, elements 130 might be fabricated from metal and joined to base portion 50 during holder fabrication. Note in FIG. 5A that some of the bundles 20 are shown as having a hexagon cross-section, other bundles 20' are shown with a circular cross-section. It is understood that openings 40 and bias alignment mechanisms 120 may be provided for a variety of different cross-sections to accommodate differently shaped bundles 20, 20', if required.

The cross-sectional view of FIG. 5B depicts cooperation between prong elements 130, the axis of openings 40, and the longitudinal axis of the bundle 20, 20' that is retained. In FIG. 5B, ends 30 of the retained bundles are shown as protruding through and beyond the lower surface (in FIG. 5B) of holder 50. In many applications it is desired to planarize what is shown in FIG. 5B as surface 30. This process typically involves machining steps such as lapping and polishing. The result is shown in FIG. 5C in which surface 30' is substantially flush with the lower surface (in the orientation of FIG. 5C) of holder 50. Distal ends 60 will have typically been treated to form concave well regions 64, with each well region ideally receiving one bead 62.

FIG. 5D depicts holder 50 and retained bundles 20, 20' with the beaded distal bundle ends 60 in alignment with and disposed within well regions 230 formed on a well plate (also called a microtiter plate) 220. Each well region 230 is partially filled with a solution 240 containing an analyte. Ideally the angle θ between the longitudinal axis of each retained bundle 20 and the plane of holder 50 will be 90°. However in FIG. 5D the leftmost bundle is shown as having somehow been skewed in its alignment such that θ'<90°. However a few degrees of misalignment is nonetheless acceptable using holder 50, providing that the beaded end of the misaligned bundle does not physically strike the interior of its associated well region 230 such that beads are damaged, or are not adequately in contact with the well solution 240.

Those skilled in the relevant art will appreciate that solution 240 in the individual wells 230 will contains a target analyte, and that different wells may have different solutions. In FIG. 5D, while beaded bundle ends 60 are within their associated well solutions (e.g., solution in a well whose location is registerably aligned with the particular bundle in the array retained by holder 50), the bundles may be excited with optical energy from optical system 70 (or 70' in a suitable configuration). Depending upon the nature of the excitation energy, the target analyte within a solution in a given well may change the optical response of the associated bead 62, which response may be observed using optical system 70 (or 70'). Alternatively in other applications, optical excitation and analysis occurs after the beaded ends of the various bundles are removed from the solution containing wells. However it will be appreciated that it is important that the beaded ends of the bundles in an array retained by holder 50 must align with their intended well 230 to expose the retained beads to the desired solution 240 within the intended well.

FIG. 6A is a top perspective view of a holder 50 in which an array of fiber optic bundles 20 are retained in openings 40' formed in the holder. Whereas the holder of FIGS. 1–3B providing retaining openings 40 that had uniform diameter D per opening, holder 50 in the embodiment of FIGS. 6A–6D preferably utilizes stepped retaining openings 40'. Referring to FIG. 6D, by stepped opening it is meant that each opening 40' has a small diameter (or transverse dimension) region slightly larger than dimension D of the retained bundle 20 as the bottom of the opening, but a larger diameter (or transverse dimension) D' at the top of the opening. The larger D' portion of the opening 40' extends downward (in the orientation of FIGS. 6A, 6C and 6D) a depth Tx≦T, where T is thickness of holder 50. As best seen in FIG. 6D, the enlarge d typically annular region surrounding bundle 20 in the D' region is filled with a potting compound 45, to help secure bundle 20 in a desired orientation, e.g., normal to the plane of holder 50. Many materials can be used as potting compound 45, but preferably the material selected will not emit substantial fluorescence that could degrade signal/noise ratio of the signals to be detected by optical system 70 or 70'. If desired, an alignment jig may be used to retain the free distal ends (ends 60) of bundles 20 during the time compound 45 hardens. FIG. 6D shows distal ends 60 of the various strands 22 within a bundle 20 as including beads 26. Typically beads will be attached after potting compound 45 has been added and allowed to harden.

Figure 9A:
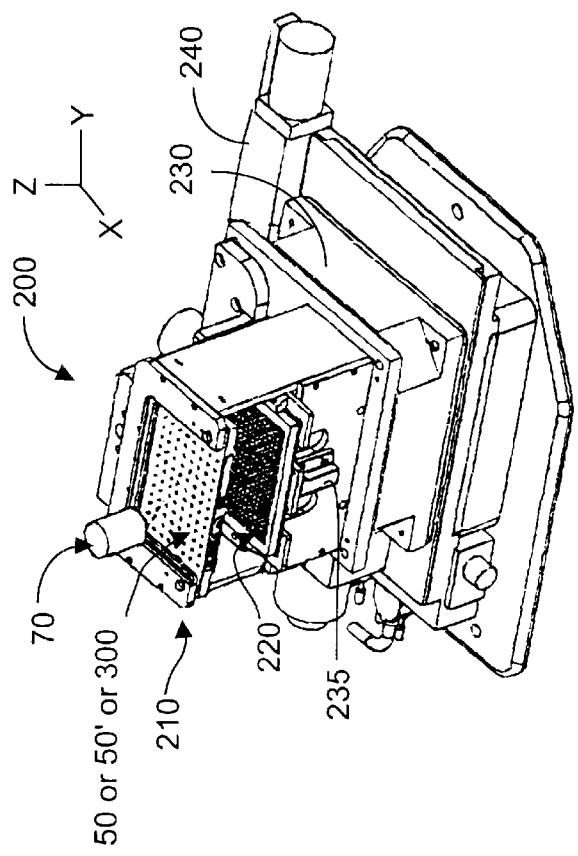
FIGS. 9A and 9B are perspective views of docking stations adapted to retain holders, according to the present invention, for solution sampling and/or optical imaging.
Figure 9B:
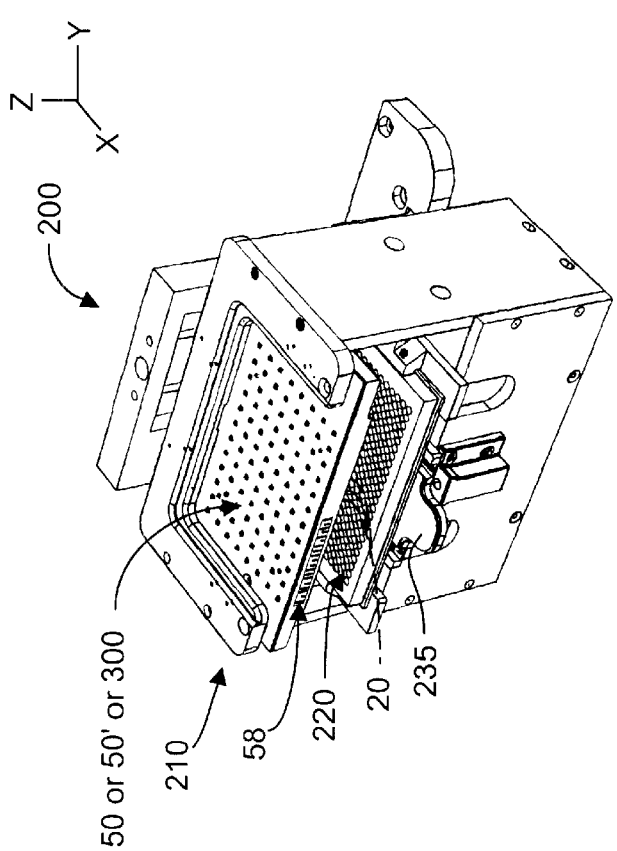

Note in FIGS. 6A–6C that holder 50 preferably includes various mechanisms that will be used to help self-align the holder within a docking-type station used for obtaining data and/or for imaging (See FIGS. 9A and 9B.) Such alignment mechanisms include projecting pegs 52, 52', projecting faces 54, 54', recesses 56, and guide slots 59. If desired, each holder 50 or 50' may have attached a label 58 that may include information, barcoded or otherwise, identifying the bundles 20, the production lot number, etc.

Figure 7A:
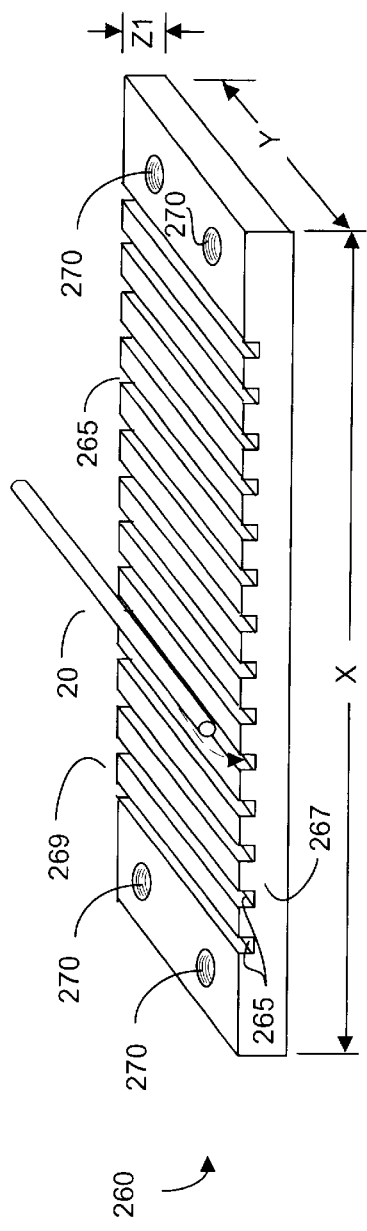
FIG. 7A is a perspective view of a module used in a modularly formed fiber optic bundle holder, according to the present invention.
Figure 7B:
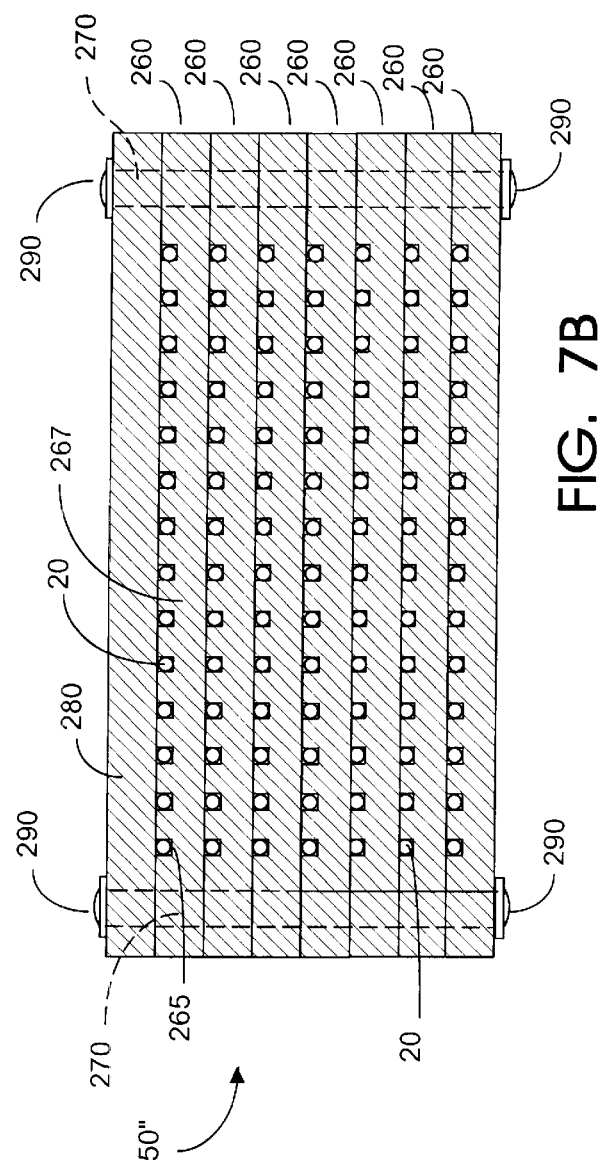
FIG. 7B is a top view of a fiber optic bundle holder comprising modules such as shown in FIG. 7A, according to the present invention.

Referring now to FIGS. 7A and 7B, a modular comb-like holder 50" to retain, temporarily or permanently, an array of fiber optic bundles 20 is comprised of grooved or channeled module members 260, held together by retaining mechanisms 290 inserted through openings 270 formed in each member 260. FIG. 7A depicts a module member 260 having length X, width Y, and thickness Z1. Typically X will be on the order of a few inches (e.g., several cm), dimension Y will be less than or equal to the length L of a fiber optic bundle 20 to be inserted and retained within a groove or channel 265 formed in member 260. The Z1 thickness of member 260 will be greater than the transverse dimension of the fiber optic bundle 20 to be seated within the groove or channel formed in member 260. The transverse dimension of bundle 20 will be the diameter for a bundle 20 having a circular cross-section, and will be the maximum cross-dimension for another cross-section shape.

FIG. 7A depicts a bundle 20 being inserted into a groove 65. If bundle 20 has length L (measured along the bundle longitudinal axis) and it is desired to have the bundle protrude a distance Δ from front surface 267 of member 260, the member dimension Y will be approximately Y=(L−Δ). Once the grooves in member 260 have been filled with respective bundles 20, the bundle ends adjacent member rear surface 269 can be made flush (if desired) with that surface, for example by aligning against a flat plane held parallel to surface 269. This will cause the oppose bundle end (typically the beaded end) to protrude a desired distance Δ from front surface 267. Of course if desired Δ could be zero. For ease of illustration channels 265 are shown as being square in cross-section. However if some (or all) bundles 20 had a cross-sectional shape not readily retained by a square profile channel, the corresponding channel could be milled or otherwise formed to conform better to such bundle cross-sections. Such alternative channel cross-sections could, without limitation, be circular, elliptical, rectangular, triangular, polygonal, and so forth. Since the beads deposited in wells in the strands comprising bundles 20 often carry their own unique identification tags, some degree of rotational movement of a bundle within its channel can be tolerated.

FIG. 7B depicts seven element members 260, whose grooves 265 have been filled with associated bundles 20, and an ungrooved but similarly dimensioned member 280 compressively held together by two screw/bolt or other retaining mechanisms 290. Screws 290 pass through openings 270 formed in each member 260 and ungrooved member 270 and compressively retain members 260 and member 270 together to form the laminated or modular holder 50". In FIG. 7B, holder 50" retains an array comprising 14 columns and 7 rows of bundles, or a total of 98 bundles. Since each bundle may comprise many thousands of individually beaded fiber optic strands, holder 50" indeed retains an array of arrays. Holder 50" may be used as a permanent holder, or as a temporary holder. For example, holder 50" might be employed as temporary holder 80 in the embodiment of FIG. 4A, and after bundles 20 are further secured (e.g., by solidified material 90'), members 260 and 270 may be loosened and removed from the otherwise retained bundles.

Thus far holders have been described that could readily accommodate retaining a plurality of fiber optic bundles, e.g., retaining an array of arrays. In some instances it may be sufficient or desirable to work with a single fiber optic bundle 20, rather than with a plurality of bundles. Although the holders thus far described could be used to retain a single bundle, the embodiment of FIGS. 8A and 8B is designed to do precisely that.

Figure 8B:
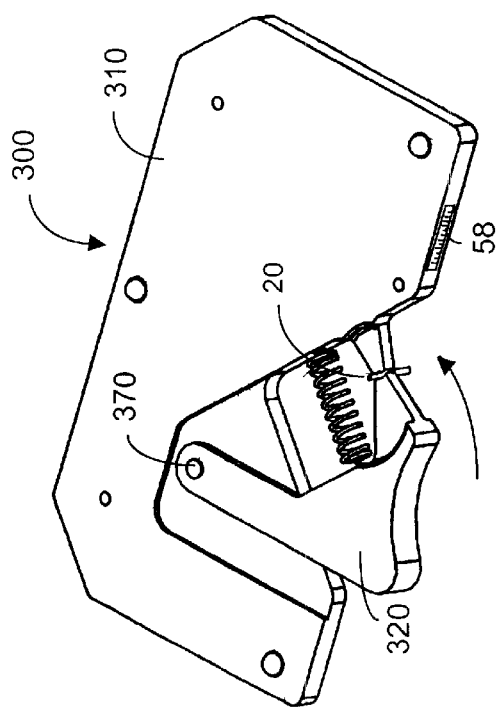
FIGS. 8A and 8B are perspective views of a holder adapted to retain a single fiber optic bundle, according to the present invention.
Figure 8A:
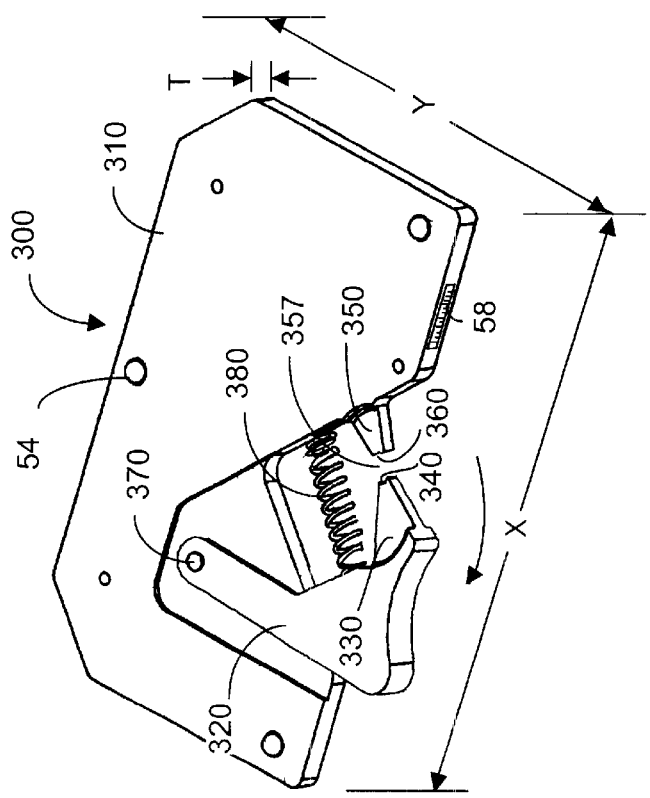

FIGS. 8A and 8B depict a holder 300 comprising a substantially planar stationary body member 310 and a pivotably attached movable member 320. Movable member 320 includes a region 330 whose distal end 340 is shaped to accommodate approximately half the cross-section of a single bundle 20. In similar fashion, stationary member 310 includes a region 350 whose distal end 360 is also shaped to accommodate approximately half the cross-section of a single bundle 20. Movable member 320 is attached by a pivot mechanism 370 to stationary member 310 such that distal regions 340 and 360 can meet. A bias mechanism such as spring 380 urges movable member 320 to pivot towards fixed member 310 such that the normal state for holder 50 is that distal portions 340 and 360 tend to meet each other.

In FIG. 8A, movable member 320 is shown as being pivoted away about pivot mechanism 370, in the direction of the curved arrow, from stationary member 310, e.g., by a user's hand, which is not shown. Accordingly there is now a gap 357 between distal portions 340 and 360. When holder 300 is in the position shown in FIG. 8A, a fiber optic bundle 20 is inserted into gap 357, and bias mechanism 380 is permitted to close the gap such that regions 340 and 360 securely clamp around and retain bundle 20. FIG. 8B depicts the normal, retaining, state for holder 310, in which the curved arrow indicates the relative movement of member 320 due to the bias created by mechanism 380. Overall dimensions X, Y, and T for holder 300 may be similar to what has been stated for the multiple bundle holders described with respect to FIGS. 1–7B.

Holder 300 preferably is made from a relatively rigid and durable material such as metal or plastic. If member portions 330 and 360 are not formed integrally with members 320 and 310 respectively, such portions should be formed from a material that will not emit substantial fluorescence. Although a spring is depicted as an exemplary bias mechanism 380, other mechanisms could instead be used, including for example an elastic band, or perhaps magnets disposed in members 320 and 310 to attract distal portions 340 and 360 together magnetically.

FIG. 9A depicts what might be termed a docking station 200, with which bundles 20 retained in a probe holder 50', or 50, or a single bundle 20 retained in holder 300, according to the present invention, may be used. The probe holder is retained by a generally U-shaped member 210 that is sized to receive most or all of three sides of the holder. In the orientation shown in FIG. 9A, the portion of bundle(s) 20 that emerge from the holder (e.g., the Δ lengths) are pointed downward. Disposed beneath the array of downwardly pointed bundles is a so-called well plate 220 that will provide an individual recess or well for each bundle 20 retained by holder 50', 50, or 300. Thus, if the holder retains a number of rows equal to R, and a number of columns equal to C, well plate 220 will provide at least R×C wells. These wells will be disposed in rows and columns such that if the distance along the Z-axis separating the and bundle ends 60 were reduced, one bundle would fit into a corresponding well. In practice, R×C=96 is a commonly used number of wells, but more or fewer wells (and corresponding bundles) could instead be used.

As noted, individual wells typically hold a target analyte containing solution, in which each well need not hold the identical solution. As shown in FIG. 9B, a Z-axis stage 230 is energized by a motor or by manual means (not shown) such that the distance separating the wells and the distal bundle ends is reduced to approach zero. In the preferred embodiment the elevation of well plate 220 is raised while the probe holder 50' remains stationary, but the holder could be moved while the well plate remained stationary, or the well plate and the probe holder could each be moved along the Z-axis. A Z-axis latch 235 may be provided to lock Z-axis movement once the interface between the beaded ends of the bundles and the well solutions is attained.

While the beaded probe tips are within the well solutions, the bundles may be excited with optical energy from optical system 70 (or 70' in a suitable configuration). The optical system can detect any response of individual beads 62 to the excitation to determine what analyte(s) might be present within the associated well. Normally docking station 200 includes an X-axis, Y-axis stage mechanism 240 to enable optical system 70 (or 70') to be moved incrementally to examine each bundle and more specifically each beaded fiber within a bundle.

Alternatively in other applications, optical excitation and analysis occurs after the beaded ends of the various bundles are removed from the solution containing wells. Although FIGS. 9A and 9B depict a preferred implementation of a docking station 200, other configurations could also be used with probe holders according to the present invention.

It will be appreciated that bundles of fiber optic strands may undergo processing before or after being retained in a holder according to the present invention. For example, bundle(s) may be inserted into a holder before of after polishing and/or etching of the bundle end(s). The bundle(s) may be retained in the holder before or after insertion of the typically beaded bundle ends into solution containing wells, or after such insertion. Typically the bundles will have been retained in a holder according to the present invention before imaging or other analytical read-out process.

Providing different embodiments of holders that share a common form factor permits retaining any of the holders in a common docking station apparatus. Further, the consistent registration providing by holders according to the present invention permits inserting and removing the bundle retaining holders from such docking station for such intermediate processing as may be required and carried out external to a docking station. It will be appreciated that the holder may be attached to bundles at time of holder fabrication, or subsequently, or a holder may be provided to retain (in a desired perpendicular orientation) a single bundle. Providing holders that may be manually held enables experimenters o easily grasp and manipulate the bundle(s) retained by the holder. Further, holders with such form factor help protect the retained bundles and help avoid soiling or contaminating the bundle ends by minimizing inadvertent contact with the bundle ends. In summary, the present invention meets many needs that have hitherto gone unfulfilled in the prior art.

Once made, the compositions of the invention find use in a variety of applications, including the detection of target analytes, particularly amplification reactions, as described in PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; and an application filed on Apr. 21, 2000, entitled "Detection of Nucleic Acid Reactions on Bead Arrays" (no serial number received yet), all of which are expressly incorporated by reference. Modifications and variations may be made to the disclosed embodiments without departing from the subject and spirit of the invention as defined by the following claims.

What is claimed is:

1. A holder for at least one fiber optic bundle, comprising:
    a base having an upper surface and an a lower surface, spaced-apart from each other a distance T;
    opening defined in said upper surface penetrating substantially perpendicularly toward said lower surface a depth Th, where Th$\leq$T, said opening having a cross-section sized to retain one end of said bundle; and
    means, formed integrally with said base, for biasedly retaining said bundle in said holder perpendicular to a plane of said base;
    wherein a bundle having a first end inserted into said opening is retained by said holder such that a longitudinal axis of said bundle is retained substantially perpendicular to a plane of said first surface.

2. The holder of claim 1, further including:
    an array of openings defined in said upper surface penetrating substantially perpendicularly toward said lower surface a depth Th, where Th$\leq$T, each said opening having a cross-section sized to retain one end of a bundle of fiber optics;
    wherein an array of bundles of fiber optics, each having a first end inserted into one said opening, is retained by said holder in registration such that a longitudinal axis of each said bundle is substantially perpendicular to a plane of said first surface.

3. The holder of claim 1, wherein Th=T, and the inserted said first end of said bundle has a bundle surface substantially flush with said second surface of said holder.

4. The holder of claim 3, wherein:
    said bundle has a length L$\approx$T; and
    a second end of the inserted said bundle has a bundle surface substantially flush with said first surface of said holder.

5. The holder of claims 1, wherein said holder is fabricated from a material selected from a group consisting of (a) glass, (b) plastic, (c) stainless steel, (d) epoxy, and (e) thermosetting epoxy.

6. The holder of claim 1, wherein said holder has at least one characteristic selected from a group consisting of (a) said thickness T is 0.5 mm$\leq$T$\leq$1 cm, (b) said bundle has a length L, and T$\geq$0.1 L, (c) said opening has a transverse dimension D in a range of about 0.5 mm$\leq$D$\leq$15 cm, (d) said opening defines at least one cross-sectional shape selected from a group consisting of (i) circular, (ii) oval, (iii) rounded, (iv) square, (v) rectangular, (vi) a polygon, (vii) and a shape partially rounded and partially straight, and (d) said base is fabricated from a material selected from a group consisting of (i) metal, (ii) glass, (iii) ceramic, (iv) plastic, (v) epoxy, (vi) thermosetting epoxy, and (vii) wax.

7. The holder of claim 1, wherein said opening includes a region selected from a group consisting of (a) a region that frictionally retains a portion of said bundle, (b) an enlarged annular region surrounding a portion of said bundle, (c) an enlarged region into which adhesive can be added, and (d) an enlarged region into which potting compound can be added.

8. A holder for at least one fiber optic bundle, comprising:
    a base having an upper surface and an a lower surface, spaced-apart from each other a distance T;
    an opening defined in said upper surface penetrating substantially perpendicularly toward said lower surface a depth Th, where Th$\leq$T, said opening having a cross-section sized to retain one end of said bundle; and
    means for biasedly retaining said bundle in said holder perpendicular to a plane of said base, wherein said means is formed separately from said base but is attached to said base;
    wherein a bundle having a first end inserted into said opening is retained by said holder such that a longitudinal axis of said bundle is retained substantially perpendicular to a plane of said first surface.

9. The holder of claim 8, further including:
    array of openings defined in said upper surface penetrating substantially perpendicularly toward said lower surface a depth Th, where Th$\leq$T, each said opening having a cross-section sized to retain one end of a bundle of fiber optics;
    wherein an array of bundles of fiber optics, each having a first end inserted into one said opening, is retained by said holder in registration such that a longitudinal axis of each said bundle is substantially perpendicular to a plane of said first surface.

10. The holder of claim 8, wherein Th=T, and the inserted said first end of said bundle has a bundle surface substantially flush with said second surface of said holder.

11. The holder of claim 10, wherein:
    said bundle has a length L$\approx$T; and
    a second end of the inserted said bundle has a bundle surface substantially flush with said first surface of said holder.

12. The holder of claim 8, wherein said holder is fabricated from a material selected from a group consisting of (a) glass, (b) plastic, (c) stainless steel, (d) epoxy, and (e) thermosetting epoxy.

13. The holder of claim 8, wherein said holder has at least one characteristic selected from a group consisting of (a) said thickness T is 0.5 mm≦T≦1 cm, (b) said bundle has a length L, and T≧0.1 L, (c) said opening has a transverse dimension D in a range of about 0.5 mm≦D≦15 cm, (d) said opening defines at least one cross-sectional shape selected from a group consisting of (i) circular, (ii) oval, (iii) rounded, (iv) square, (v) rectangular, (vi) a polygon, (vii) and a shape partially rounded and partially straight, and (d) said base is fabricated from a material selected from a group consisting of (i) metal, (ii) glass, (iii) ceramic, (iv) plastic, (v) epoxy, (vi) thermosetting epoxy, and (vii) wax.

14. The holder of claim 8, wherein said opening includes a region selected from a group consisting of (a) a region that frictionally retains a portion of said bundle, (b) an enlarged annular region surrounding a portion of said bundle, (c) an enlarged region into which adhesive can be added, and (d) an enlarged region into which potting compound can be added.

15. A holder for at least one fiber optic bundle, comprising:

a base having an upper surface and an a lower surface, spaced-apart from each other a distance T;

an opening defined in said upper surface penetrating substantially perpendicularly toward said lower surface a depth Th, where Th≦T, said opening having a cross-section sized to retain one end of said bundle; and at least one bias element disposed on said first surface adjacent said opening, said bias element having at least one characteristic selected from a group consisting of (a) said base and said bias element are integrally formed from injected plastic, (b) said bias element is formed separately from said base, (c) said bias element includes a metal strip a portion of which projects upright from said base, (d) said bias element includes a plastic strip a portion of which projects upright from said base;

wherein a bundle having a first end inserted into said opening is retained by said holder such that a longitudinal axis of said bundle is retained substantially perpendicular to a plane of said first surface.

16. The holder of claim 15, further including:

an array of openings defined in said upper surface penetrating substantially perpendicularly toward said lower surface a depth Th, where Th≦T, each said opening having a cross-section sized to retain one end of a bundle of fiber optics;

wherein an array of bundles of fiber optics, each having a first end inserted into one said opening, is retained by said holder in registration such that a longitudinal axis of each said bundle is substantially perpendicular to a plane of said first surface.

17. The holder of claim 15, wherein Th=T, and the inserted said first end of said bundle has a bundle surface substantially flush with said second surface of said holder.

18. The holder of claim 17, wherein:

said bundle has a length L≈T; and a second end of the inserted said bundle has a bundle surface substantially flush with said first surface of said holder.

19. The holder of claim 15, wherein said holder is fabricated from a material selected from a group consisting of (a) glass, (b) plastic, (c) stainless steel, (d) epoxy, and (e) thermosetting epoxy.

20. The holder of claim 15, wherein said holder has at least one characteristic selected from a group consisting of (a) said thickness T is 0.5 mm≦T≦1 cm, (b) said bundle has a length L, and T≧0.1 L, (c) said opening has a transverse dimension D in a range of about 0.5 mm≦D≦15 cm, (d) said opening defines at least one cross-sectional shape selected from a group consisting of (i) circular, (ii) oval, (iii) rounded, (iv) square, (v) rectangular, (vi) a polygon, (vii) and a shape partially rounded and partially straight, and (d) said base is fabricated from a material selected from a group consisting of (i) metal, (ii) glass, (iii) ceramic, (iv) plastic, (v) epoxy, (vi) thermosetting epoxy, and (vii) wax.

21. The holder of claim 15, wherein said opening includes a region selected from a group consisting of (a) a region that frictionally retains a portion of said bundle, (b) an enlarged annular region surrounding a portion of said bundle, (c) an enlarged region into which adhesive can be added, and (d) an enlarged region into which potting compound can be added.

22. A modular holder for a plurality of fiber optic bundles, said bundles having a transverse dimension D and having a length L, the modular holder comprising:

plurality of planar modules having an upper surface and an a lower surface, spaced-apart from each other a distance T, and having at least one side of length Lx≦said L; each of said modules defining at least two channels, each of said channels sized to retain within at least a portion of one of said bundles; and each of said modules defining at least one through opening sized to admit a compression-creating member such that a stack of said planar modules, and said bundles retained by said channels, can be retained to form said modulator holder;

wherein said modular holder retains said bundles such that a longitudinal axis of each said bundle is substantially parallel to a longitudinal axis of at least one other of said bundles.

23. The modular holder of claim 22, said planar modules have at least one characteristic selected from a group consisting of (a) said length 5 mm≦L≦200 mm, (b) said dimension 0.01 mm≦D≦100 mm, (c) Lx=L, (d) said planar modules are formed from a material selected from a group consisting of (i) metal, (ii) plastic, (iii) glass, (iv) epoxy, (v) thermosetting epoxy, and (d) a cross-section of said channels has a shape selected from a group consisting of (i) circular, (ii) oval, (iii) rounded, (iv) square, (v) rectangular, (vi) a polygon, and (vii) a shape partially rounded and partially straight.

24. The modular holder of claim 22, further including at least one said retaining member, wherein a length of said retaining member determines how many said planar modules are retained in said modular holder.

* * * * *